US005922338A

United States Patent [19]

Brich et al.

[11] Patent Number: 5,922,338

[45] **Date of Patent: *Jul. 13, 1999**

[54] POLYOL ESTERS, THEIR PREPARATION AND USE IN DEPOT FORMS OF PHARMACOLOGICALLY ACTIVE AGENTS

[75] Inventors: Zdenek Brich, Binningen, Switzerland; Thomas Kissel, Ehrenkirchen, Germany

[73] Assignee: Novartis AG, Basel, Switzerland

[ * ] Notice: This patent is subject to a terminal disclaimer.

[21] Appl. No.: 08/471,304

[22] Filed: Jun. 6, 1995

Related U.S. Application Data

[62] Division of application No. 07/834,018, Feb. 11, 1993, which is a continuation of application No. 07/525,271, May 17, 1990, abandoned, which is a continuation of application No. 07/263,747, Oct. 28, 1988, abandoned, which is a continuation of application No. 06/878,943, Jun. 26, 1986, abandoned, which is a continuation of application No. 06/643,836, Aug. 23, 1984, abandoned.

[30] Foreign Application Priority Data

Aug. 26, 1983 [CH] Switzerland ............................ 4671/83

[51] Int. Cl.[6] ............................ A61F 13/00; A61K 9/48; A61K 31/70; C07H 13/00

[52] U.S. Cl. ............................ 424/422; 424/451; 514/23; 514/25; 514/53; 514/54; 536/115; 536/119

[58] Field of Search .................................... 536/115, 119; 514/23, 25, 53, 54; 424/78, 422, 451

[56] References Cited

U.S. PATENT DOCUMENTS

| | | | |
|---|---|---|---|
| 4,104,464 | 8/1978 | James | 536/115 |
| 4,130,639 | 12/1978 | Shalaby et al. | 424/78 |

*Primary Examiner*—Elli Peselev
*Attorney, Agent, or Firm*—Hesna J. Pfeiffer

[57] ABSTRACT

This invention provides a polyester of a polyol, said polyol containing at least 3 hydroxyl groups and having a molecular weight of up to 20,000 at least 1 hydroxyl group in said polyol being in the form of an ester, with a poly- or co-poly-lactic acid residue, each having a molecular weight of at least from 5,000. These are useful for parenteral depot formulations.

6 Claims, No Drawings

POLYOL ESTERS, THEIR PREPARATION AND USE IN DEPOT FORMS OF PHARMACOLOGICALLY ACTIVE AGENTS

This is a division of application Ser. No. 07/834,018, filed Feb. 11, 1993, which in turn is a continuation of application Ser. No. 07/525,271, filed May 17, 1990 which in turn is a continuation of application Ser. No. 07/263,747, filed Oct. 28, 1988, which in turn is a continuation of application Ser. No. 06/878,943, filed Jun. 26, 1986, which in turn is a continuation of application Ser. No. 06/643,836, filed Aug. 23, 1984, the latter four of which are now abandoned.

The invention relates to novel esters especially polyol esters, with polymeric hydroxycarboxylic ester residues, their preparation and use e.g. in the production of depot forms of pharmacologically active agents.

A broad class of polyol esters having polymeric hydroxycarboxylic ester residues are disclosed from the German Patent No. 1.020.034 in which glycerol esters having polylactide ester residue of 30 lactic acid residues or pentaerythritol ester with polylactic acid residue of 16 lactic acid residues are specifically described. The patent does not specifically disclose any longer chain polymer esters of polyols having at least three hydroxyl groups.

These products are used as solvents, e.g. for pharmaceutical purposes, as emulgators or as additives for synthetic materials and plastics. There is no disclosure of their use for pharmaceutical depot matrix compositions.

Esters from sugar alcohols, e.g. from erythritol, xylitol, ribitol and sorbitol with poly-ϵ-hydroxycapronic acid are described in Journal of Polymer Science, Polymer Chemistry Edition, Vol. 20, 319–326, especially at 323–326 (1982).

The molecular weight of these esters depends on the extent of esterification of the hydroxyl groups of the polyol esters and on the length of the poly-ϵ-hydroxycapronic acid residues. Its order of magnitude is from about 26000 to 65000.

The esters exhibit a star polymer structure, their single polyol residue as the central part being surrounded by acid residue chains. No use of the polyol esters is mentioned in the publication.

The diffusion velocity of pharmacologically active agents from the ester and the degradation velocity of the ester as a matrix material for active agents are too small for practical use as an implant or microcapsule. Due to the hydrophobic properties of the poly-ϵ-hydroxycapronic acid residues the esters are not suitable as matrix materials for depot forms of pharmacologically active agents.

Several depot forms of pharmacologically active agents have been proposed in the literature. In the European application No. 92918, are disclosed polypeptides in a matrix of an ester of e.g. polyvinyl alcohol (M.W. 14000) or polyethylene glycol (M.W. 6000 or 20,000) containing polymer hydroxycarboxylic ester residues, e.g. from lactic acid (M.W. 26,000 to 114,000) and sometimes additionally glycolic acid (M.W. 10,000).

However, matrix materials having high molecular proportions of such polyol radicals have too hydrophilic properties and become degraded under use conditions too quickly.

Additionally, the strong hydrophilic properties and softness of the matrix materials hinder their production, the further processing and the use of depot forms, especially microcapsules.

As esters are additionally mentioned, e.g. dextrane as a polyol, but due to the high molecular weights of the dextranes such ester formation is practically impossible.

Depot forms of pharmacologically active agents in a matrix of a polymer of polyols and hydroxy carboxylic acids are proposed as part of a very broad class of products in the International application WO 78/00011 (PCT). However, polymers of polyol and hydroxy monocarboxylic acids are not exemplified. Exemplified are depot forms from a polyol ester containing polymeric dicarboxylic acid residues, e.g. of tartaric acid.

These polyol esters have a structure different from the products described above. They have a linear chain and contain alternatively polyol residues and dicarboxylic acid residues.

The formed esters have such a low solubility, and soluble precondensates must be formed in order to incorporate the pharmacologically active agents. Only then can the precondensated active agent containing matrix materials be condensed further.

If saturated dicarboxylic acids, such as tartaric acid are used, it is stated that the final total condensation must be carried out at an elevated temperature (about 170–200° C.) which is not suitable for heat-sensitive active agents.

Using pentaerythritol as a polyol, strongly cross-linked products are formed, which are not suitable for incorporating pharmacologically active agents and which do not degrade in vivo sufficiently fast.

The mass degradation rate for depot -formulations made from these materials is too slow.

The manufacturing process disclosed to produce the microcapsules or other depot forms is also tedious.

The known matrix polymers of the art generally have a disadvantageous short or long degradation period under conditions of use, e.g. in the body, compared with the required release period of the pharmacologically active agents causing the active agents either to disappear prematurely with the matrix material or to be disappeared completely from the still present polymer matrix. Accordingly an additional dosage of the depot form cannot be administered subsequently, since an undesired accumulation of the polymeric matrix material may occur.

The present invention sets out to overcome the above disadvantages and to provide a useful pharmaceutical depot form for clinical use.

Furthermore the depot forms made from the polyol esters according to the invention may have the advantage of a drug release time which is satisfactorily longs e.g. 1 month, and a short degradation period of the mass thereafter. They are suitable for the incorporation of a large variety of e.g. water soluble or hydrophobic active agents.

Additionally, the polyol esters of the invention may be easy handled and be easily worked up to incorporate the active agents and to produce pharmaceutical composition forms, e.g. microcapsules and implants. These microcapsules are not soft; consequently, they are easy to administer through an injection needle.

The present invention provides an ester of a polyol, said polyol containing at least 3 hydroxyl groups and having a molecular weight of up to 20,000 at least 1 hydroxyl group in said polyol being in the form of an esters with a poly- or co-poly-lactic acid residue each having a molecular weight of from 5,000 e.g. to 85,000. In another aspect the present invention provides a reaction product of a polyol containing at least 3 hydroxyl groups and having a molecular weight of up to 20,000 or a reactive derivative thereof and lactic acid or a reactive derivative thereof and if desired at least a second hydroxycarboxylic acid or a functional derivative thereof, the product having a polymer chain of molecular weight of at least 5,000. These products are indicated as polyol esters of the invention.

The polyol residues are particularly of a polyol containing a chain of carbon atoms. A special polyol form is such having a linear structure and containing 3 to 6, particularly 6 hydroxyl groups. Suitable polyols having a linear structure include e.g. mannitol, pentaerythritol, sorbitol, ribitol and xylitol. Another preferred polyol form is one having a cyclic structure and containing 4 to 30 hydroxyl groups.

The polyols of a cyclic structure contain particularly one or more saccharide units and with at least 3 hydroxyl groups per unit. Examples of such polyols are those with a fructose structure, e.g. fructose itself. Particular polyols with cyclic structure are those having glucose structure, e.g. glucose itself, or having 2 to 8 glucose units. These units are preferably connected in 1,4 and/or 1,6-position, especially in 1,4-position. A polyol containing more glucose units, connected in 1,4-position, is e.g. β-cyclodextrine.

The preferred polyol is glucose.

The polyol esters may have e.g. a polyol residue with at least 2 or 3 hydroxyl groups in the form of esters, which contain poly-lactide or co-poly-lactide chains. Their structures may be thus branched, i.e. star shaped. Preferably each such chain has the same hydroxycarboxylic acid residue.

The chains may contain lactide residues alone. Alternatively they may contain additionally e.g. one, two, three or more specific hydroxycarboxylic acid residues, e.g. up to 70 Mol %, e.g. 30–70%.

Preferred extra residues are glycolic acid residues. Preferably up to 70 Mol %, e.g. 30–70%, especially 50 Mol % glycolic acid units are present. Instead of or in addition to the glycolic acid units other different units may be present, e.g. ϵ-hydroxycapronic acid units, preferably up to 20 Mol %.

The lactic acid units may be present in optical pure form (D- or L-lactide form) or as their mixtures, e.g. their racemic form (D,L-lactide form).

The present invention also provides a process for the production of a product of the invention characterized in that a polyol of a molecular weight of up to 20,000 and having at least 3 hydroxyl groups or a reactive derivative thereof is esterified with lactic acid or a reactive derivative thereof or additionally with at least a second hydroxycarboxylic acid or a functional derivative thereof.

Preferably the process is characterized in that a polyol of a molecular weight of up to 20,000 and having at least 3 hydroxyl groups, is reacted with lactic acid or additionally with at least a second hydroxycarboxylic acid in lactone- or dimeric cyclic ester form, in the presence of a catalyst, which makes a ring opening polymerization feasible.

The catalyst is preferably Sn-octoate.

The reaction components are e.g. mixed together with the catalyst and reacted at an elevated temperature.

If a solvent is present, e.g. toluene, the components may be reacted at the reflux temperature of the solvent. Without a solvent the reaction temperature can be higher, e.g. if glucose is used as a polyol, up to about 170° and if β-cyclodextrine is used, up to 180°. Preferably the reaction is effected in the absence of water.

The formed polyol ester of the invention may be purified and isolated in a conventional manner.

The determination of the molecular weight of the purified product may be effected using conventional methods, preferably by gelpermeation-chromatography (GPC) using polystyrene as standard (Mw), Dupont Ultrastyragel 500 Angstrom and 10000 Angstrom as the column and tetrahydrofuran as a solvent, at room temperature.

The molecular weights Mw of the polyol esters according to the invention are preferably between 20,000 and 200,000, e.g. between 20,000 and 80,000.

The molecular weights of the polyol esters of the invention are dependent on the weight ratio of the components in the reaction and on the reaction conditions, e.g. the reaction temperature (see Example 8). A lower reaction temperature may lead to shorter polymer chains and thus to lower molecular weight polyol esters.

The isolation and purification may influence the molecular weight of the purified polyol ester. Changing the isolation and purification conditions leads to a change of the molecular weight (see Example 2). Since the polyol ester may exist generally in fact as a mixture of molecules with chains of a different length the composition of this mixture may be influenced by isolation and purification methods, such as extraction, filtration and the isolation and purification liquids and their amounts and the isolation and purification temperature.

The molecular weight of the purified polymer may be increased by removing low molecular weight compounds, e.g. by a suitable precipitation of the polymer, e.g. in methanol, or by a membrane filtration.

The amount of components having lower molecular weights may be reduced by membrane filtration to such an extent, that in the molecular weight spectrums determined by GPC, their peaks altogether have a height of up to 10%, preferably up to 7% of the height of the peak Mw of the polymer.

The invention thus also provides a products wherein in the GPC any separate low molecular weight peaks comprise altogether up to 10% of the height of the peak Mw of the polyester.

The polyol esters of the invention are particularly suitable to incorporate active agents and produce sustained release effects of the active agents in the body.

The balance of hydrophobic and hydrophilic factors—the polyol residue represents the hydrophilic and the poly lactide or co-poly lactide residue the hydrophobic factor—can be regulated by changing the polyols, the extent of esterification of the hydroxyl groups, the chain length of the polymeric chains and the identity and the relative amounts of the specific hydroxycarboxylic acid units in the chain.

The polyol esters according to the invention are therefore particularly suitable for the preparation of pharmaceutical depot formulations containing pharmacologically active agents. Such depot formulations may exist as a polyol ester matrix containing the active agent. Preferred depot forms are implants (e.g. for subcutaneous administration) and microcapsules (e.g. for oral or particularly for parenteral, e.g. intramuscular administration).

The present invention therefore also provides a pharmaceutical depot form, having a matrix of the ester of the invention, containing a pharmacologically active agent.

The depot forms are novel and form part of the invention.

The depot forms may be made in conventional manner, the polyol esters according to the invention being easy to handle and often incorporating a high concentration of active agent.

In order to produce microcapsules, the active agent may be dissolved in a volatile solvent, such as methylene dichloride. A solution of the polyol ester, e.g. in the same solvent, may then be added and the resulting mixture may be sprayed into air while carefully regulating the temperature and then dried to form microcapsules. Alternatively the active agent may be dissolved or suspended, e.g. in methylene dichloride, and the polyol ester may be dissolved in a volatile, water immiscible solvent, e.g. methylene dichloride, after which the organic phase may then be mixed vigorously with a stirred aqueous solution, e.g. buffered to pH 7, optionally containing e.g. gelatin as an emulsifier. The organic solvent may then be removed from the resultant emulsion and the resultant microcapsules be filtered off or separated by centrifuging, washed, e.g. in a buffer, and dried.

In order to produce implants the active agent may be mixed with the polyol ester and dissolved in a volatile solvent. The solvent may be evaporated and the residue ground up. An extrusion may be formed in conventional manner, which is then pressed e.g. as implant tablets of 5 to 15, especially 7 mm, and of 20–80 mg, e.g. 20–25 mg matrix material at 75° C. and 80 bar during 10 to 20 min.

Depending on the active agent, the microcapsules may take up an average of up to 60% by weight of the active agent. The implants are preferably prepared in such a manner that they contain up to 60, e.g. 1 to 20%, by weight of the active agent.

For the active agent Bromocriptine, microcapsules may be prepared containing at most 25%, especially up to 18% and implants containing up to 18% by weight of the active agent.

The microcapsules may have a diameter from a few submicron to a few millimeters, For pharmaceutical microcapsules diameters of at most about 250 microns, e.g. 10 to 60 microns, are strived for, in order to facilitate passage through an injection needle.

The depot formulation according to the invention may be used to administer a wide variety of classes of active agents, e.g. pharmacologically active agents such as contraceptives, sedatives, steroids, sulphonamides, vaccines, vitamins, anti-migraine drugs, enzymes, bronchodilators, cardiovascular drugs, analgesics, antibiotics, antigens, anti-convulsive drugs, anti-inflammatory drugs, anti-parkinson drugs, prolactin secretion inhibitors, anti-asthmatic drugs, geriatics and anti-malarial drugs.

The depot formulations may be used for the known indications of the particular active agent incorporated therein.

The exact amounts of active agent and of the depot formulation to be administered depends on a number of factors, e.g. the condition to be treated, the desired duration of treatment, the rate of release of active agent and the degradability of the polymer matrix.

The desired formulations may be produced in known manner. The amount of the pharmacologically active agent required and the release rate thereof may be determined on the basis of known in vitro or in vivo techniques, described e.g. in Examples 26–29, e.g. how long a particular active agent concentration in the blood plasma remains at an acceptable level. The degradability of the matrix may also be obtained by in vitro or especially in vivo techniques, for example wherein the amount of matrix materials in the muscle is weighed after particular time periods.

The depot formulations of the invention may be administered in the form of e.g. microcapsules, e.g. orally preferably subcutaneously or intramuscularly, preferably in the form of or in a suspension in a suitable liquid carrier or in the form of implants, e.g. sub-cutaneously.

Repeated administration of the depot formulations of the invention may be effected when the polyol ester matrix has sufficiently degraded, e.g. after 1 month.

Examples of doses for the preferred compounds are:

For prolactin secretion inhibition with bromocryptine, for example an i.m. depot formulation may be produced which daily provides 2.5 to 7.5 mg bromocryptine over about 30 days and contains for example 70 to 230 mg bromocryptine mesylate.

For the treatment of bronchial asthma with ketotifen, for example an i.m. depot formulation may be produced which daily provides 0.5 to 0.8 mg ketotifen over about 30 days and contains for example 15 to 25 mg ketotifen.

For the reactivation of cerebral metabolism with codergocrine, for example an i.m. depot formulation may be produced which daily provides 0.1 to 0.4 mg co-dergocrine in about 30 days and contains about 3 to 12 mg.

Depot formulations for other active agents may be formulated in analogous manner, e.g. to provide the known appropriate, e.g. therapeutics concentration of active agent for parenteral use over an extended period of time, e.g. 30 days.

As indicated above the polymer degradation may be followed in in vivo and in vitro experiments, described in Examples 24 and 25. It may be seen that the polyol esters of the invention degrade faster than corresponding known polylactide and poly-lactide/glycolide acids and especially a faster degradation may be seen in the early stage, e.g. up to 30 days, especially in the case of poly-lactide/glycolide polymer chains.

Membrane filtration results in residual polymer products having in general in the early stage, especially up to 30 days, a smaller mass degradation rate as that of the corresponding non-filtered product. In the case of residual polyol esters of the invention, the degradation may be over 50% up to 30 days, and in the case of the Example 6 as described hereinafter about 70%. After 40 to 50 days it may be practically complete.

In in vitro and in vivo release rate tests the polyol esters of the invention may release the active agent at the same rate order as for corresponding known polymeric poly- or co-poly-lactides, e.g. in 30 days.

The active agents may be released mainly by diffusion from the matrix and only to a small extent by degradation of the matrix material.

This results in a more regular rate of release of active agent.

An advantage of the polyester matrices of the invention in that after a practically complete release of active agent they may be quickly degraded to an acceptable size, which may be transported by the body fluids from the site of administration.

Accordingly the present invention provides a parenteral pharmaceutical depot formulation for use as an implant or microcapsules containing a pharmacologically active agent embedded or encapsulated in a polymer matrix, said formulation being adapted to release all or substantially all the active material over an extended period of time and the polymer being adapted to degrade sufficiently to be transported from the site of administration within 20 days after release of all or substantially all the active agent.

In the following examples all temperatures are in degrees Centigrade and uncorrected.

HYFLO is a known filtering aid.

Polyol ester from D(+)-glucose, DL-dilactide and diglycolide

EXAMPLE 1

79.4 g (.0.684 Mol) of diglycolide, 120.6 g (0.838 Mol) of DL-dilactide and 0.4 g (2.2 mMol) of D(+)-glucose (0.2%)

were placed in a 1.5 l flask and heated, while stirring to 135° in an argon atmosphere after which 1 ml of Sn-octoate was added.

The reaction is exothermic. The temperature increases to 172°. After 5 minutes, stirring is discontinued and the brown viscous mixture is reacted further at 130–140° for 17 hours. After cooling, 500 ml of methylene dichloride was added. The mixture was dissolved as much as possible by boiling and the solvent was separated. This procedure was repeated after which the residue was extracted additionally with 500 methylene dichloride. The combined dark-brown solutions (in total 1500 ml) were purified with 50 g Hyflo, concentrated to 500 ml and treated with 500 ml of a 10% aqueous HCl-solution to remove the catalyst. The solution was washed five times with 500 ml of water to pH 4.5 and diluted to 1 l with methylene dichloride.

The solution was treated with $MgSO_4$ and with Hyflo, concentrated to 500 ml and added dropwise within half an hour to 3 1 of methanol at −60° C. At this temperature the mixture was stirred for 3 hours. Then the product was filtered off and dried at 40° C. in vacuo.

The molecular weight was determined by gel permeation chromatography (GPC):

Mw=34 800 Mn=19 600 Mw/Mn=1.77

Acid number: 6.8

Non-reacted lactide: 1.7%

Non-reacted glycolide:<0.4%

Molar ratio glycolide/lactide in the polymeric chains: 45/55 NMR: 360 MHz; ($CDCl_3$)

5.20 (m, 0.55 H, —CH— lactic acid)

4.82 (m, 0.9 H, —$CH_2$—glycolic acid)

1.58 (m, 3 H, —$CH_3$—lactic acid)

IR: ($CH_2Cl_2$)

$cm^{-1}$ 2950 (w,$CH_3$); 1760 (s,—COOR); 1390 and 1420 (w,$CH_3$); 1160 (s,—O—); 1090 (s,—O—).

EXAMPLES 2–5

In a manner analogous to that of Example 1, the following polyolesters were prepared:

Comments on Example 2:

Prepared to show by analysis that the glucose was incorporated into the polymer and that indeed a polyolester was formed.

Measures were taken to intensify the NMR-signal of the glucose. The glucose was a $C^{13}$—uniform marked glucose with 98.3 atom percent $C^{13}$ (LOT No.2358-4 MSD ISOTOPES, Merck, Canada).

The NMR-signal of the $C^{13}$—glucose starting material was compared with the signal of the $C^{13}$—glucose ester:

$C^{13}$-Glucose

NMR $C^{13}$ ppm 9.7.13 (d,C-1β); 93.32 (d,C-1α); 77.63 (t,C-5β); 76.92 (t,C-3β); 75.57 (t,C-2β); 73.84 (t,C-3α); 72.92 (t,C-2α); 72.24 (t,C-5α); 71.07 (t,C-4α); 70.63 (t,C-4β); 61.95 (dxd, C-6αβ).

$C^{13}$—Glucose ester of Example 2:

NMR $C^{13}$ ppm 91.80 (m, C-1β); 89.84 (m, C-1α); 72.51 - 66.73 (m, C-2,3,4,5α,β); 62.90 (m, C-6).

Since the glucose signals all are broad multiplets, it is assumed, that the glucose was practically completely incorporated. Mol ratio lactide/glycolide/glucose=32.3/66.7/0.2.

Comments on Example 3:

GPC-determination with simultaneous UV and radioactivity determination was used for the analysis of these products.

It is observed that the radioactivity of the test sample is proportionally distributed over the whole range of molecular weights, and that both the retention times in the UV and the radioactivity determination are equal.

The radioactivity of the test sample is about 30% of the predicted value, indicating that about 0.06% of the glucose was incorporated (it was started with 0.2%)

EXAMPLE 6

The product of Example 4 was dissolved in methylene dichloride and purified by a membrane filtration under a pressure of 2 atm.

Amicon apparatus

Membrane: DDS 6000 MWCO

Type FS 81 PP

Flow velocity: 2 2 ml/min

| Ex. | Polyol | DL-Di-lactide | Digly-colide | Sn-Octoate | React. temp. | Mw Mn | Mw/Mn | Mol ratio lactide/glycolide | Acid number | Non reacted lactide and glycolide |
|---|---|---|---|---|---|---|---|---|---|---|
| 2* | 4 mg $C^{13}$-D(+)-glucose (0, 2%) | 1.2 g | 0.8 g | 10 μl | — | 31,400<br>17,300 | 1.81 | — | — | — |
| 3* | 3.85 mg (D+)-glucose + 0.15 mg D(+)-1$C^{14}$-glucose | " | " | " | — | 26.400<br>10,600 | 2.50 | — | — | — |
| 4 | 0.2 g D(+)-glucose (0.2%) | 60.3 g | 39.7 g | 0.5 ml | 168° | 34,600<br>20,700 | 1.67 | 55/45 | 5.7 | 0.6%<br><0.4 & |
| 5 | 0.2 g D(+)-glucose (0.2%) | " | " | " | 155° | 23,600<br>13,300 | 1.77 | 58/42 | 8, 0 | <0, 4%<br><0, 2% |

* For analytical purposes, see following commentary.

The end volume was 2000 ml.

| Residue: | From NMR: |
|---|---|
| Mw = 42 200, Mn = 31 300, $\frac{Mw}{Mn}$ = 1.35 | $\frac{\text{lactide}}{\text{glycolide}} = \frac{53}{47}$ (Mol ratio) |
| Acid number 3.4<br>non reacted lactide <0.2%<br>non reacted glycolide <0.4% | |

| Filtrate | From NMR: |
|---|---|
| Mw = 21 600, Mn = 13 600, $\frac{Mw}{Mn}$ = 1.58 | $\frac{\text{lactide}}{\text{glycolide}} = \frac{53}{46}$ (mol ratio) |
| Acid number 10.1<br>non reacted lactide 1.2%<br>non reacted glycolide <0.4% | |

EXAMPLE 7

39.7 g (0.342 Mol) of diglycolide, 60.3 g (0.419 Mol) dilactide and 0.2 g (1.1 mMol) D(+)-glucose (0.2%) and 40 ml of toluene are heated in a 750 ml flask, while stirring to boiling temperature (108°) after which 0.5 ml Sn-octoate are added. The reaction is slightly exothermic. The temperature was raised to 112°. After 3 hours, stirring was discontinued and the brown viscous mixture was reacted further three days at 110°. After cooling 500 ml of methylene dichloride were added and the mixture was diluted at boiling temperature, purified with Hyflo and filtered.

The solution was evaporated to dryness, the residue dissolved in methylene dichloride and shaked with 400 ml of a 5% aqueous HCl solution. The solution was washed four times with 400 ml of water to pH 5 and diluted to 1 l with methylene dichloride.

The solution was dried with $MgSO_4$ and evaporated to dryness in vacuo at 40° C., The residue was dried in vacuo at 40°.

Molecular weight; Mw=32 200; Mn=18 400; Mw/Mn=1.75.

NMR and IR: As in Example 1.

EXAMPLE 8

In a manner analogous to Example 7, the following polyolester was prepared in 345 ml of toluene.

EXAMPLE 9

In an analogous manner as described in Example 6 the following product was prepared by membrane filtration from the product of Example 8:

Flow velocity: 1 ml/min
The end volume was 2200 ml

| Residue | From NMR: |
|---|---|
| Mw = 26 200, Mn = 18 000, $\frac{Mw}{Mn}$ = 1.45 | $\frac{\text{lactide}}{\text{glycolide}} = \frac{62}{37}$ (mol ratio) |
| Acid number 4.0<br>non reacted lactide <0.2%<br>non reacted glycolide <0.4% | |

| Filtrate: | From NMR: |
|---|---|
| Mw = 12 200, Mn = 3 000, $\frac{Mw}{Mn}$ = 3.75 | $\frac{\text{lactide}}{\text{glycolide}} = \frac{60}{40}$ (mol ratio) |
| Acid number 9.7<br>non reacted lactide <0.2%<br>non reacted glycolide <0.4% | |

Polyol ester from β-cyclodextrine, DL-dilactide and diglycolide

EXAMPLE 10

26.1 g of diglycolide, 39.6 g of DL-dilactide and 0.635 g β-cyclodextrine were heated in a 500 ml flask, while stirring to 140°, in a nitrogen atmosphere after which 0.125 ml of Sn-octoate was added. The reaction is distinctly exothermic. The temperature was raised to 180°. After 10 minutes, stirring was discontinued and the brown viscous mixture was reacted further at 140° for 17 hours.

The purification and isolation were carried out in an analogous manner as described in Example 1.

Molecular weight (GPC): Mw=75 700; Mn=72 300; Mw/Mn=1.05.

Non reacted lactide: 2%

Non reacted glycolide: <0.4%

Mol ratio glycolide/lactide in the polymeric chains: 47/53

NMR and IR: As in Example 1.

EXAMPLES 11–12

In an analogous manner as described in Example 3, the following polyol esters were prepared:

In a manner analogous to Example 7, the following polyolester was prepared in 345 ml of toluene

| Ex. Polyol | DL-ii-lactide | diglycolide | Sn-octoate | react. temp. | Mw Mn | $\frac{Mw}{Mn}$ | Mol ratio $\frac{\text{lactide}}{\text{glycolide}}$ | acid-number | non reacted lactide/glycolide |
|---|---|---|---|---|---|---|---|---|---|
| 80.6 g D(+)-glucose (0.2%) | 180.9 g | 119.1 g | 1.5 ml | 114.1° | 20,000<br>12,000 | 1.66 | — | 7.2 | <0.1%<br><0.4% |

In an analogous manner as described in Example 3, the following polyol esters were prepared

| Ex. | polyol | Dl-di-lactide | di-gly-colide | Sn-octoate | react. temp. | Mw / Mn | Mw/Mn | mol ratio lactide/glycolide | acid number | non reacted lactide, glycolide |
|---|---|---|---|---|---|---|---|---|---|---|
| 11 | 0.63 g β-cyclo-dextrine | 39.6 g | 26.1 g | 0.13 ml | 165.8° | 16,200<br>5,100 | 3.18 | 54/46 | 1.7 | <0.2%<br><0.4% |
| 12 | 0.63 g β-cyclo-dextrine dried at 120° in vacuo | " | " | " | 163.9° | 24,100<br>10,700 | 2.26 | 53/47 | 6.2 | <0.2%<br><0.4% |

EXAMPLE 13

The product of Example 10 was treated in an analogous manner as described in Example 6. The filtration pressure was however raised to 3 atm.

| Flow velocity 0.2 ml/min. | |
|---|---|
| Residue: | From NMR: |
| Mw = 72 200, Mn = 59 800, $\frac{Mw}{Mn} = 1.20$ | $\frac{\text{lactide}}{\text{glycolide}} = \frac{53}{47}$ (mol ratio) |
| Acid number 1.0 | |
| Filtrate: | From NMR: |
| Mw = 27 100, Mn = 15 500, $\frac{Mw}{Mn} = 1.75$ | $\frac{\text{lactide}}{\text{glycolide}} = \frac{52}{48}$ (mol ratio) |
| Acid number 21.2 | |

EXAMPLE 14

The product of Example 10 was treated in an analogous manner as described in Example 6. The filtration pressure was however raised to 2 atm.

| Flow velocity 0.3 ml/min | |
|---|---|
| Residue: | Filtrate: |
| Mw = 76 700, Mn = 72 300, $\frac{Mw}{Mn} = 1.06$ | Mw = 67 900, Mn = 47 600, $\frac{Mw}{Mn} = 1.43$ |

EXAMPLE 15

Equal amounts of the residues of the Examples 13 and 14 led, after intermediate dissolution in methylene dichloride, to a mixture of the following formation:

Mw = 70 000
Mn = 51 600 $\frac{Mw}{Mn} = 1.36$

EXAMPLES 16–17

Polyol ester from D(−)mannitol, DL-dilactide and di-glycolide

In an analogous manner as described in Example 1, the following polyol esters were prepared:

| Ex. | polyol | Dl-di-lactide | digly-colide | Sn-octoate | react. temp. | Mw / Mn | Mw/Mn | Mol ratio lactide/glycolide | acid number | non reacted lactide and glycolide |
|---|---|---|---|---|---|---|---|---|---|---|
| 16 | 0.1 g D(−) mannitol (0.2%) | 30.15 g | 19.85 g | 0.25 ml | 177.5° | 23,500<br>13,200 | 1.78 | 54/46 | 6.2 | <0.1%<br><0.4% |
| 17* | 5.0 g D(−)-mannitol (10%) | " | " | " | 176.5° | 3,500<br>3,000 | 1.13 | 54/46 | 1.4 | <0.2%<br><0.4% |

*for analytical purposes, see further comments.

EXAMPLES 18–23

Polyol esters from other polyols, DL-dilactide and diglycolide

In an analogous manner as described in Example 1, the following polyol esters were prepared:

In an analogous manner as described in Example 1, the following polyol esters were prepared

| Ex. | polyol | Dl-di-lactide | digly-colide | Sn-octoate | react. temp. | Mw / Mn | Mw / Mn | Mol ratio lactide / glycolide | acid number | non reacted lactide and glycolide |
|---|---|---|---|---|---|---|---|---|---|---|
| 18 | 0.5 g penta-erythritol (1%) | 30.15 g | 19.85 g | 0.25 ml | 132.5° | 14,800 / 10,000 | 1.49 | 54 / 46 | 7.5 | 0.4% / 0.1% |
| 19* | 5 g penta-erythritol (10%) | " | " | " | 154.5° | 2,740 / 2,450 | 1.12 | | 0.73 | |
| 20 | 0.1 g sorbi-tol (0.2%) | " | " | " | 179.1° | 35,600 / 20,500 | 1.74 | 57 / 43 | | |
| 21 | 0.1 g ribitol (0.2%) | " | " | " | 159.7° | 16,080 / 6,800 | 2.38 | | | <0.1% / <0.4% |
| 22 | 0.1 g xylitol (0.2%) | " | " | " | 156.6° | 15,600 / 6,000 | 2.60 | | | <0.1% / <0.4% |
| 23 | 0.1 g D(−)-fructose (0.2%) | " | " | " | 175° | 21,900 / 12,700 | 1.73 | 54 / 46 | | |

*for analytical purposes see comments after

Comments on Example 17:

NMR (in $CDCl_3$) δ(ppm) 5.23 (m, —CH— of lactic acid, 1 H); 4.83 (m, —$CH_2$— of glycolic acid, 1.73 H); 4.46 - 4.17 (m, —CH— and —$CH_2$— of mannitol and of the terminal lactic- or glycolic acid units.

Mol ratio: lactide/glycolide/mannitol=1:0.86:0.08. This corresponds to a Mw of 1530 (however in the signal 4.46-4.17 are also included the terminal lactic- or glycolic acid units).

Used amount mannitol $672\times10^{-4}$ Mol %; incorporated amount $526\times10^{-4}$ Mol %.

Comments on Example 19:

NMR (in $CDCl_3$)

δ(ppm) 5.23 (m, —CH— of lactic acid, 1 H); 4.9-4.65 (m, —$CH_2$ of glycolic acid, 1.5 H); 4.45-4.10 (m, —$CH_2$— of pentaerythritol and —CH— and —$CH_2$— of the terminal lactic acid or glycolic acid units, 1 H); 1.58 (m, $CH_3$ of lactic acid, 3 H).

Mol ratio lactide/glycolide/pentaerythritol: 1:0.75:0.15 (however in the signal 4.45-4.10 are also included the terminal lactic- or glycolic acid units).

Used amount pentaerythritol $960\times10^{-4}$ Mol %, incorporated amount (from NMR)=$1000\times10^{-4}$ Mol % (the signals at 4.45 - 4.10 ppm do not exclusively relate to pentaerythritol).

Determination of the degradation of polyol ester in vitro

EXAMPLE 24

30 to 80 μm thick films are molded from 5% solutions of the polyol ester of Example 6 in methylene dichloride. The films are dried for 50 hours at 40° in vacuo, thereafter several days in an desiccator containing $P_2O_5$.

300 mg of the film, divided into little pieces were added to 30 ml of distilled water and shaken at 37° (50 rpm). The amount of polymer was determined periodically by filtration and weighing.

EXAMPLE 25

Implants in the form of tablets of 7 mm diameter and of 23–25 mg, pressed from a polyol ester granulate of Example 6 at 80 bar and 75° for 10 min., were implanted i.p. in rats. After a certain period they were extracted from the tissue with methylene dichloride, and thereby separated from organic tissue material, evaporated to dryness and weighed.

Release of active agents from polyol ester matrices in vitro

EXAMPLE 26

Release tests were carried out with microcapsules, which contained bromocriptine as active agent. The microcapsules were prepared according to the above described spray drying method with the following parameters:

| | |
|---|---|
| Bromocriptine mesylate | 2.6 g |
| Matrixpolymer of Example 9 (residue) | 10.0 g |
| Methylene dichloride | 100 ml |
| Spray conditions (NIRO equipment) | |
| Temperature of the input | 50° C. |
| Temperature of the ouput | 40° C. |
| Air pressure | 2 atm |
| Influx | 32 ml/min |

After their preparation the microcapsules were dried for 48 hours. at 30° in a low vacuum, sieved (<180 um) and washed with citrate buffer at pH 3. The microcapsules contained 17.9% of the active agent.

After repeated drying in low vacuum (48 hours, 35°, 0.1 bar) and sieving (<180 um) the microcapsules were gammasterilized at 2.5 Mrad.

The release was measured photometrically at 301 nm at 25° C. in citrate buffer pH 4 as an extraction medium, poured freshly through the microcapsules with a flow velocity of 2.5 ml/min.

Over a period of 24 hours about 62% of the active agent was regularly released.

N.B. The release in vitro was measured at pH 4 because of better solubility of bromocryptine at this pH.

EXAMPLE 27

Release tests were carried out with microcapsules, which contained codergocrine as a active agents.

The microcapsules were prepared according to the above described emulsion process with the following parameters:

| | |
|---|---|
| Codergocrine base | 7 g |
| Matrix polymer of example 5 | 13 g |
| Methylene dichloride | 40 ml |
| Ethanol 94% | 30 ml |

Emulsifying conditions:

Volume ratio organic phase/aqueous phase: 1:65

Rotation speed of the turbine p=3100 rpm

The release was measured as described in Example 26.

EXAMPLE 28

The process of Example 27 was carried out with the following parameters:

| | |
|---|---|
| Ketotifen base | 5 g |
| Matrix polymer of example 5 | 15 g |
| Methylene dichloride | 80 ml |

Emulsifying conditions:

Volume ratio organic phase/aqueous phase: 3:130 p=2000 rpm

Stirring time: 2 hours

The microcapsules contained 16.5% Ketotifen.

EXAMPLE 29

Release of active agents from polyol ester matrices in vivo

Release tests were carried out with microcapsules, which contained bromocriptine as active agent.

The microcapsules were prepared according to the above described spray drying process in the NIRO-spray drying apparatus, equipped with a centrifugal spray gun. The matrix polymer consisted of the product of Example 4 and contained 17.8% bromocriptine.

An amount of these microcapsules, corresponding to 5.0 mg bromocriptine-mesylate, in a vehicle of 0.2 ml of sodium carboxymethylcellulose, was injected in the right thigh muscle of a rabbit. Periodically blood was taken from the rabbit during 21 days.

The blood levels of the medicine were measured by a specific radioimmunoassay and had a mean value of 1.6 ng/ml (A.U.C.=33.0). The blood levels were practically all between 1.20 and 1.80 ng/ml.

We claim:

1. A branched polyglycolide lactide ester of glucose, having a molecular weight of from 20,000 to 200,000.

2. The ester of glucose of claim 1 having a molecular weight of 20,000 to 80,000.

3. A formulation comprising a matrix of said ester of glucose of claim 1 and a therapeutically effective amount of a pharmacologically active agent.

4. A formulation of claim 3 wherein said active agent is selected from the group consisting of bromocriptine, ketotifen and co-dergocrine.

5. A formulation of claim 3 wherein said formulation is in implant form.

6. A formulation of claim 3 wherein said formulation is in microcapsule form.

* * * * *